United States Patent [19]

Kisida et al.

[11] Patent Number: 4,914,116
[45] Date of Patent: Apr. 3, 1990

[54] NITROGEN-CONTAINING HETEROCYCLIC COMPOUNDS, AND THEIR USE AS INSECTICIDES

[75] Inventors: Hirosi Kisida, Tokyo; Sumio Nishida, Takarazuka, both of Japan; Makoto Hatakoshi, Seattle, Wash.

[73] Assignee: Sumitomo Chemical Company, Limited, Osaka, Japan

[21] Appl. No.: 335,274

[22] Filed: Apr. 10, 1989

Related U.S. Application Data

[62] Division of Ser. No. 100,308, Sep. 23, 1987, Pat. No. 4,847,259, which is a division of Ser. No. 868,716, May 30, 1986, Pat. No. 4,714,706.

[30] Foreign Application Priority Data

May 20, 1985 [JP]  Japan ............................... 60-117189

[51] Int. Cl.⁴ .................. A61K 31/38; A61K 31/435; A61K 31/505; C07D 277/34
[52] U.S. Cl. ..................... 514/369; 514/274; 514/345; 544/315; 544/318; 546/291; 546/301; 546/302; 546/303; 548/182; 548/186
[58] Field of Search ............... 548/182, 186; 514/369

[56] References Cited

U.S. PATENT DOCUMENTS 3,551,417  12/1970  Symon et al. ..................... 514/369

*Primary Examiner*—Mary C. Lee
*Assistant Examiner*—J. Richter

[57] ABSTRACT

A nitrogen-containing heterocyclic compounds are representable by the formula:

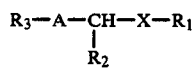

wherein $R_1$ is either one of the following groups:

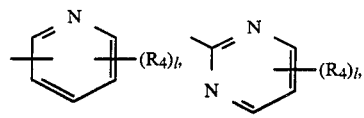

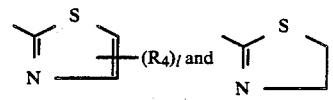

(in which $R_4$ is a hydrogen atom, a halogen atom or a methyl group and $l$ is an integer of 1 or 2);
$R_2$ is a hydrogen atom or a methyl group;
$R_3$ is an alkyl group, an alkoxy group, an alkenyl group or an alkenyloxy group, all of which may have optionally one or more substituents;
A is either one of the following groups:

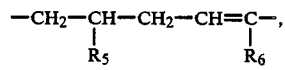

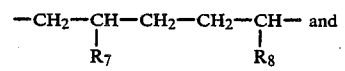

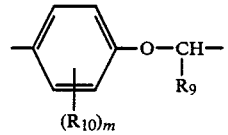

(in which $R_5$, $R_6$, $R_7$, $R_8$ and $R_9$ are, the same or different, each a hydrogen atom or a methyl group, $R_{10}$ is a hydrogen atom, a halogen atom or a lower alkyl group and m is an integer of 1 to 4); and
X is an oxygen atom or a sulfur atom,
which is useful as an insecticidal agent.

16 Claims, No Drawings

NITROGEN-CONTAINING HETEROCYCLIC COMPOUNDS, AND THEIR USE AS INSECTICIDES

This application is a divisional of copending application Ser. No. 07/100,308, filed on 9/23/87 U.S. Pat. No. 4,847,259, which is a divisional application of Ser. No. 06/868,716, filed May 30, 1986, and now U.S. Pat. No. 4,714,706, which issued Dec. 22, 1987.

The present invention relates to nitrogen-containing heterocyclic compounds, and their production and use.

The nitrogen-containing heterocyclic compounds of the invention are representable by the formula:

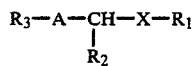

wherein
$R_1$ is either one of the following groups:

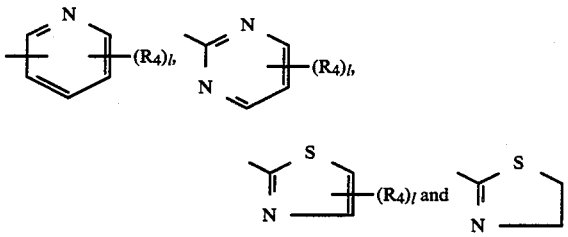

(in which $R_4$ is a hydrogen atom, a halogen atom or a methyl group and l is an integer of 1 or 2);
$R_2$ is a hydrogen atom or a methyl group;
$R_3$ is an alkyl group, an alkoxy group, an alkenyl group or an alkenyloxy group, all of which may have optionally one or more substituents;
A is either one of the following groups:

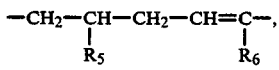

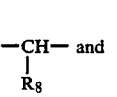

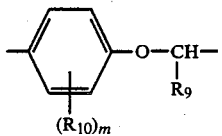

(in which $R_5$, $R_6$, $R_7$, $R_8$ and $R_9$ are, the same or different, each a hydrogen atom or a methyl group, $R_{10}$ is a hydrogen atom, a halogen atom or a lower alkyl group and m is an integer of 1 to 4); and
X is an oxygen atom or a sulfur atom.

In the above significances, an alkyl group, an alkoxy group, an alkenyl group and an alkenyloxy group represented by the symbol $R_3$ may have usually not more than 8 carbon atoms and are particularly preferred to indicate alkyl of 1 to 7 carbon atoms, alkoxy of 2 to 7 carbon atoms, alkenyl of 3 to 7 carbon atoms and alkenyloxy of 3 to 7 carbon atoms, respectively. Further, all of them may have optionally one or more substituents.

Examples of the alkyl group include methyl, ethyl, propyl, isopropyl, butyl, sec-butyl, tert-butyl, isobutyl, pentyl, isopentyl, neopentyl, 1-methylbutyl, 2-methylbutyl, 1,1-dimethylpropyl, 1,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, 1-ethylbutyl, 2-ethylbutyl, heptyl, 1-methylhexyl, 2-methylhexyl, 3-methylhexyl, 4-methylhexyl, 5-methylhexyl, 1,1-dimethylpentyl, 1,2-dimethylpentyl, 1,3-dimethylpentyl, 1,4-dimethylpentyl, 2,2-dimethylpentyl, 2,3-dimethylpentyl, 2,4-dimethylpentyl, 3,3-dimethylpentyl, 3,4-dimethylpentyl, 4,4-dimethylpentyl, 1,1,2-trimethylbutyl, 1,1,3-trimethylbutyl, 1,2,2-trimethylbutyl, 1,2,3-trimethylbutyl, 1,3,3-trimethylbutyl, 2,2,3-trimethylbutyl, 2,3,3-trimethylbutyl, 1,1,2,2-tetramethylpropyl, 1-ethylpentyl, 2-ethylpentyl, 3-ethylpentyl, 1-ethyl-1-methylbutyl, 1-ethyl-2-methylbutyl, 1-ethyl-3-methylbutyl, 2-ethyl-1-methylbutyl, 2-ethyl-2-methylbutyl, 2-ethyl-3-methylbutyl, 1-propylbutyl, 1,1-diethylpropyl, etc.

Examples of the alkoxy group are ethyloxy, propyloxy, isopropyloxy, butyloxy, sec-butyloxy, tert-butyloxy, isobutyloxy, pentyloxy, isopentyloxy, neopentyloxy, 1-methylbutyloxy, 2-methylbutyloxy, 1,1-dimethylpropyloxy, 1,2-dimethylpropyloxy, 1-ethylpropyloxy, hexyloxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1,1,2-trimethylpropyloxy, 1,2,2-trimethylpropyloxy, 1-ethylbutyloxy, 2-ethylbutyloxy, heptyloxy, 1-methylhexyloxy, 2-methylhexyloxy, 3-methylhexyloxy, 4-methylhexyloxy, 5-methylhexyloxy, 1,1-dimethylpentyloxy, 1,2-dimethylpentyloxy, 1,3-dimethylpentyloxy, 1,4-dimethylpentyloxy, 2,2-dimethylpentyloxy, 2,3-dimethylpentyloxy, 2,4-dimethylpentyloxy, 3,3-dimethylpentyloxy, 3,4-dimethylpentyloxy, 4,4-dimethylpentyloxy, 1,1,2-trimethylbutyloxy, 1,1,3-trimethylbutyloxy, 1,2,2-trimethylbutyloxy, 1,2,3-trimethylbutyloxy, 1,3,3-trimethylbutyloxy, 2,2,3-trimethylbutyloxy, 2,3,3-trimethylbutyloxy, 1,1,2,2-tetramethylpropyloxy, 1-ethylpentyloxy, 2-ethylpentyloxy, 3-ethylpentyloxy, 1-ethyl-1-methylbutyloxy, 1-ethyl-2-methylbutyloxy, 1-ethyl-3-methylbutyloxy, 2-ethyl-1-methylbutyloxy, 2-ethyl-2-methylbutyloxy, 2-ethyl-3-methylbutyloxy, 1-propylbutyloxy, 1,1-diethylpropyloxy, etc.

The term "alkenyl" may be construed in a broad sense and covers those having one or more double bonds. Therefore, examples of the alkenyl group include allyl, isopropenyl, 1-propenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1,3-pentadienyl, 2,4-pentadienyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1-ethyl-1-propenyl, 1-ethyl-2-propenyl, 1-ethyl-2-propenyl, 2-ethyl-2-propenyl, 1-hexenyl, 2-hexenyl, 3-hexenyl, 4-hexenyl, 5-hexenyl, 1,3-hexadienyl, 2,4-hexadienyl, 3,5-hexadienyl, 1,3,5-hexatrienyl, 1-methyl-1-pentenyl, 2-methyl-1-pentenyl, 3-methyl-1-pentenyl, 4-methyl-1-pentenyl, 1-methyl-2- pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1-methyl-1,3-pentadienyl, 2-methyl-1,3-pentadienyl, 3-methyl-1,3-pentadienyl, 4-methyl-1,3-pentadienyl, 1-methyl-2,4-pentadienyl, 2-methyl-2,4-pentadienyl, 3-methyl-2,4-pentadienyl, 4-methyl-2,4-pentadienyl, 1,2-dimethyl-1-butenyl, 1,3-dimethyl-1-butenyl, 2,3-dimethyl-1-butenyl, 3,3-dimethyl-1-butenyl, 1,1-dimethyl-2-butenyl, 1,2-dimethyl-2-butenyl, 1,3-dimethyl-2-butenyl, 2,3-dimethyl-2-butenyl, 1,1-dimethyl-3-butenyl, 1,2-dimethyl-3-butenyl, 1,3-dimethyl-3-butenyl, 2,2-dimethyl-3-butenyl, 2,3-dimethyl-3-butenyl, 1-ethyl-1-butenyl, 2-ethyl-1-butenyl, 1-ethyl-2-butenyl, 2-ethyl-2-butenyl, 1-ethyl-3-butenyl, 2-ethyl-3-butenyl, 1,1,2-trimethyl-2-propenyl, 1-heptenyl, 2-heptenyl, 3-heptenyl, 4-heptenyl, 5-heptenyl, 6-heptenyl, 1,3-heptadienyl, 2,4-heptadienyl, 3,5-heptadienyl, 4,6-heptadienyl, 1,3,5-heptatrienyl, 2,4,6-heptatrienyl, 1-methyl-1-hexenyl, 2-methyl-1-hexenyl, 3-methyl-1-hexenyl, 4-methyl-1-hexenyl, 5-methyl-1-hexenyl, 1-methyl-2-hexenyl, 2-methyl-2-hexenyl, 3-methyl-2-hexenyl, 4-methyl-2-hexenyl, 5-methyl-2-hexenyl, 1-methyl-3-hexenyl, 2-methyl-3-hexenyl, 3-methyl-3-hexenyl, 4-methyl-3-hexenyl, 5-methyl-3-hexenyl, 1-methyl-4-hexenyl, 2-methyl-4-hexenyl, 3-methyl-4-hexenyl, 4-methyl-4-hexenyl, 5-methyl-4-hexenyl, 1-methyl-5-hexenyl, 2-methyl-5-hexenyl, 3-methyl-5-hexenyl, 4-methyl-5-hexenyl, 5-methyl-5-hexenyl, 1-methyl-1,3-hexadienyl, 2-methyl-1,3-hexadienyl, 3-methyl-1,3-hexadienyl, 4-methyl-1,3-hexadienyl, 5-methyl-1,3-hexadienyl, 1-methyl-2,4-hexadienyl, 2-methyl-2,4-hexadienyl, 3-methyl-2,4-hexadienyl, 4-methyl-2,4-hexadienyl, 5-methyl-2,4-hexadienyl, 1-methyl-3,5-hexadienyl, 2-methyl-3,5-hexadienyl, 3-methyl-3,5-hexadienyl, 4-methyl-3,5-hexadienyl, 5-methyl-3,5-hexadienyl, 1-methyl-1,3,5-hexatrienyl, 2-methyl-1,3,5-hexatrienyl, 3-methyl-1,3,5-hexatrienyl, 4-methyl-1,3,5-hexatrienyl, 5-methyl-1,3,5-hexatrienyl, 1,2-dimethyl-1-pentenyl, 1,3-dimethyl-1-pentenyl, 1,4-dimethyl-1-pentenyl, 2,3-dimethyl-1-pentenyl, 2,4-dimethyl-1-pentenyl, 3,3-dimethyl-1-pentenyl, 3,4-dimethyl-1-pentenyl, 4,4-dimethyl-1-pentenyl, 4,5-dimethyl-1-pentenyl, 1,1-dimethyl-2-pentenyl, 1,2-dimethyl-2-pentenyl, 1,3-dimethyl-2-pentenyl, 1,4-dimethyl-2-pentenyl, 2,3-dimethyl-2-pentenyl, 2,4-dimethyl-2-pentenyl, 3,4-dimethyl-2-pentenyl, 4,4-dimethyl-2-pentenyl, 1,1-dimethyl-3-pentenyl, 1,2-dimethyl-3-pentenyl, 1,3-dimethyl-3-pentenyl, 1,4-dimethyl-3-pentenyl, 2,2-dimethyl-3-pentenyl, 2,3-dimethyl-3-pentenyl, 2,4-dimethyl-3-pentenyl, 3,4-dimethyl-3-pentenyl, 1,1-dimethyl-4-pentenyl, 1,2-dimethyl-4-pentenyl, 1,3-dimethyl-4-pentenyl, 1,4-dimethyl-4-pentenyl, 2,2-dimethyl-4-pentenyl, 2,3-dimethyl-4-pentenyl, 2,4-dimethyl-4-pentenyl, 3,3-dimethyl-4-pentenyl, 3,4-dimethyl-4-pentenyl, 1,2-dimethyl-1,3-pentadienyl, 1,3-dimethyl-1,3-pentadienyl, 1,4-dimethyl-1,3-pentadienyl, 2,3-dimethyl-1,3-pentadienyl, 2,4-dimethyl-1,3-pentadienyl, 3,4-dimethyl-1,3-pentadienyl, 4,4-dimethyl-1,3-pentadienyl, 1,1-dimethyl-2,4-pentadienyl, 1,2-dimethyl-2,4-pentadienyl, 1,3-dimethyl-2,4-pentadienyl, 1,4-dimethyl-2,4-pentadienyl, 2,3-dimethyl-2,4-pentadienyl, 2,4-dimethyl-2,4-pentadienyl, 3,4-dimethyl-2,4-pentadienyl, 1,2,3-trimethyl-1-butenyl, 1,3,3-trimethyl-1-butenyl, 2,3,3-trimethyl-1-butenyl, 1,1,2-trimethyl-2-butenyl, 1,1,3-trimethyl-2-butenyl, 1,2,3-trimethyl-2-butenyl, 1,1,2-trimethyl-3-butenyl, 1,1,3-trimethyl-3-butenyl, 1,2,2-trimethyl-3-butenyl, 1,2,3-trimethyl-3-butenyl, 2,2,3-trimethyl-3-butenyl, 1,2,3-trimethyl-1,3-butadienyl, etc.

Likewise, examples of the alkenyloxy group are allyloxy, isopropenyloxy, 1-propenyloxy, 1-butenyloxy, 2-butenyloxy, 3-butenyloxy, 1-methyl-1-propenyloxy, 2-methyl-1-propenyloxy, 1-methyl-2-propenyloxy, 2-methyl-2-propenyloxy, 1-pentenyloxy, 2-pentenyloxy, 3-pentenyloxy, 4-pentenyloxy, 1,3-pentadienyloxy, 2,4-pentadienyloxy, 1-methyl-1-butenyloxy, 2-methyl-1-butenyloxy, 3-methyl-1-butenyloxy, 1-methyl-2-butenyloxy, 2-methyl-2-butenyloxy, 3-methyl-2-butenyloxy, 1-methyl-3-butenyloxy, 2-methyl-3-butenyloxy, 3-methyl-3-butenyloxy, 1,1-dimethyl-2-propenyloxy, 1-ethyl-1-propenyloxy, 1-ethyl-2-propenyloxy, 2-ethyl-2-propenyloxy, 1-hexenyloxy, 2-hexenyloxy, 3-hexenyloxy, 4-hexenyloxy, 5-hexenyloxy, 1,3-hexadienyloxy, 2,4-hexadienyloxy, 3,5-hexadienyloxy, 1,3,5-hexatrienyloxy, 1-methyl-1-pentenyloxy, 2-methyl-1-pentenyloxy, 3-methyl-1-pentenyloxy, 4-methyl-1-pentenyloxy, 1-methyl-2-pentenyloxy, 2-methyl-2-pentenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, 4-methyl-4-pentenyloxy, 1-methyl-1,3-pentadienyloxy, 2-methyl-1,3-pentadienyloxy, 3-methyl-1,3-pentadienyloxy, 4-methyl-1,3-pentadienyloxy, 1-methyl-2,4-pentadienyloxy, 2-methyl-2,4-pentadienyloxy, 3-methyl-2,4-pentadienyloxy, 4-methyl-2,4-pentadienyloxy, 1,2-dimethyl-1-butenyloxy, 1,3-dimethyl-1-butenyloxy, 2,3-dimethyl-1-butenyloxy, 3,3-dimethyl-1-butenyloxy, 1,1-dimethyl-2-butenyloxy, 1,2-dimethyl-2-butenyloxy, 1,3-dimethyl-2-butenyloxy, 2,3-dimethyl-2-butenyloxy, 1,1-dimethyl-3-butenyloxy, 1,2-dimethyl-3-butenyloxy, 1,3-dimethyl-3-butenyloxy, 2,2-dimethyl-3-butenyloxy, 2,3-dimethyl-3-butenyloxy, 1-ethyl-1-butenyloxy, 2-ethyl-1-butenyloxy, 1-ethyl-2-butenyloxy, 2-ethyl-2-butenyloxy, 1-ethyl-3-butenyloxy, 2-ethyl-3-butenyloxy, 1,1,2-trimethyl-2-propenyloxy, 1-heptenyloxy, 2-heptenyloxy, 3-heptenyloxy, 4-heptenyloxy, 5-heptenyloxy, 6-heptenyloxy, 1,3-heptadienyloxy, 2,4-heptadienyloxy, 3,5-heptadienyloxy, 4,6-heptadienyloxy, 1,3,5-heptatrienyloxy, 2,4,6-heptatrienyloxy, 1-methyl-1-hexenyloxy, 2-methyl-1-hexenyloxy, 3-methyl-1-hexenyloxy, 4-methyl-1-hexenyloxy, 5-methyl-1-hexenyloxy, 1-methyl-2-hexenyloxy, 2-methyl-2-hexenyloxy, 3-methyl-2-hexenyloxy, 4-methyl-2-hexenyloxy, 5-methyl-2-hexenyloxy, 1-methyl-3-hexenyloxy, 2-methyl-3-hexenyloxy, 3-methyl-3-hexenyloxy, 4-methyl-3-hexenyloxy, 5-methyl-3-hexenyloxy, 1-methyl-4-hexenyloxy, 2-methyl-4-hexenyloxy, 3-methyl-4-hexenyloxy, 4-methyl-4-hexenyloxy, 5-methyl-4-hexenyloxy, 1-methyl-5-hexenyloxy, 2-methyl-5-hexenyloxy, 3-methyl-5-hexenyloxy, 4-methyl-5-hexenyloxy, 5-methyl-5-hexenyloxy, 1-methyl-1,3-hexadienyloxy, 2-methyl-1,3-hexadienyloxy, 3-methyl-1,3-hexadienyloxy, 4-methyl-1,3-hexadienyloxy, 5-methyl-1,3-hexadienyloxy, 1-methyl-2,4-hexadienyloxy, 2-methyl-2,4-hexadienyloxy, 3-methyl-2,4-hexadienyloxy, 4-methyl-2,4-hexadienyloxy, 5-methyl-2,4-hexadienyloxy, 1-methyl-3,5-hexadienyloxy, 2-methyl-3,5-hexadienyloxy, 3-methyl-3,5-hexadienyloxy, 4-methyl-3,5-hexadienyloxy, 5-methyl-3,5-hexadienyloxy, 1-methyl-1,3,5-hexatrienyloxy, 2-methyl-1,3,5-hexatrienyloxy, 3-methyl- 1,3,5-hexatrienyloxy, 4-methyl-1,3,5-hexatrienyloxy, 5-methyl-1,3,5-hexatrienyloxy, 1,2-dimethyl-1-pentenyloxy, 1,3-dimethyl-1-pentenyloxy, 1,4-dimethyl-1-pentenyloxy, 2,3-dimethyl-1-pentenyloxy, 2,4-dimethyl-1-pentenyloxy, 3,3-dimethyl-1-pentenyloxy, 3,4-dimethyl-1-pentenyloxy, 4,4-dimethyl-1-pentenyloxy, 4,5-dimethyl-1-pentenyloxy, 1,1-dimethyl-2-pentenyloxy, 1,2-dimethyl-2-pentenyloxy, 1,3-dimethyl-2-pentenyloxy, 1,4-dimethyl-2-pentenyloxy, 2,3-dimethyl-2-pentenyloxy, 2,4-dimethyl-2-pentenyloxy, 3,4-dimethyl-2-pentenyloxy, 4,4-dimethyl-2-pentenyloxy, 1,1-dimethyl-3-pentenyloxy, 1,2-dimethyl-3-pentenyloxy, 1,3-dimethyl-3-pentenyloxy, 1,4-dimethyl-3-pentenyloxy, 2,2-dimethyl-3-pentenyloxy, 2,3-dimethyl-3-pentenyloxy, 2,4-dimethyl-3-pentenyloxy, 3,4-dimethyl-3-pentenyloxy, 1,1-dimethyl-4-pentenyloxy, 1,2-dimethyl-4-pentenyloxy, 1,3-dimethyl-4-pentenyloxy, 1,4-dimethyl-4-pentenyloxy, 2,2-dimethyl-4-pentenyloxy, 2,3-dimethyl-4-pentenyloxy, 2,4-dimethyl-4-pentenyloxy, 3,3-dimethyl-4-pentenyloxy, 3,4-dimethyl-4-pentenyloxy, 1,2-dimethyl-1,3-pentadienyloxy, 1,3-dimethyl-1,3-pentadienyloxy, 1,4-dimethyl-1,3-pentadienyloxy, 2,3-dimethyl-1,3-pentadienyloxy, 2,4-dimethyl-1,3-pentadienyloxy, 3,4-dimethyl-1,3-pentadienyloxy, 4,4-dimethyl-1,3-pentadienyloxy, 1,1-dimethyl-2,4-pentadienyloxy, 1,2-dimethyl-2,4-pentadienyloxy, 1,3-dimethyl-2,4-pentadienyloxy, 1,4-dimethyl-2,4-pentadienyloxy, 2,3-dimethyl-2,4-pentadienyloxy, 2,4-dimethyl-2,4-pentadienyloxy, 3,4-dimethyl-2,4-pentadienyloxy, 1,2,3-trimethyl-1-butenyloxy, 1,3,3-trimethyl-1-butenyloxy, 2,3,3-trimethyl-1-butenyloxy, 1,1,2-trimethyl-2-butenyloxy, 1,1,3-trimethyl-2-butenyloxy, 1,2,3-trimethyl-2-butenyloxy, 1,1,2-trimethyl-3-butenyloxy, 1,1,3-trimethyl-3-butenyloxy, 1,2,2-trimethyl-3-butenyloxy, 1,2,3-trimethyl-3-butenyloxy, 2,2,3-trimethyl-3-butenyloxy, 1,2,3-trimethyl-1,3-butadienyloxy, etc.

Examples of the substituent which may be present on the alkyl group, the alkoxy group, the alkenyl group and the alkenyloxy group are lower alkoxy, halo(lower-)alkoxy, halogen, nitro, amino, etc.

The term "halogen" includes fluorine, chlorine, bromine and iodine. The term "lower" is intended to mean any group having not more than 5 carbon atoms.

Organophosphorus insecticides, organochlorinated insecticides, carbamate insecticides, etc. have made a great contribution in prevention and extermination of harmful insects. Some of these insecticides, however, exhibit a high toxicity. Further, their residual effect causes sometimes unfavorable abnormality in the ecosystem of insects. Furthermore, resistance to those insecticides is noticed in house flies, planthoppers, leafhoppers, rice borers, etc.

In order to solve the above problems, an extensive study was carried out, and as the result, it has now been found that the nitrogen-containing heterocyclic compounds (I) exert a noticeable juvenile hormone-like activity and produce a remarkable preventing and exterminating effect against insects belonging to Coleoptera, Lepidoptera, Hemiptera, Dictyoptera, Diptera, etc. in agricultural fields, forest lands, granaries, stored products, sanitary facilities, etc. at relatively low concentrations.

As the insecticide having a juvenile hormone-like activity, there is known "methoprene" (U.S. Pat. Nos. 3,904,662 and 3,912,815). However, its insecticidal activity is still not satisfactory.

The nitrogen-containing heterocyclic compounds (I) can be prepared by various procedures, of which typical examples are shown below.

PROCEDURE A

A compound of the formula:

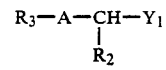

(II)

wherein $R_2$, $R_3$ and A are each as defined above and $Y_1$ is a halogen atom, a mesyloxy group or a tosyloxy group is reacted with a compound of the formula:

(III)

wherein $R_1$ and X are each as defined above or its alkali metal salt to give the nitrogen-containing heterocyclic compound (I).

PROCEDURE B

A compound of the formula:

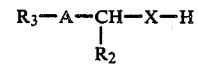

(IV)

wherein $R_2$, $R_3$, A and X are each as defined above or its alkali metal salt is reacted with a compound of the formula:

(V)

wherein $R_1$ is as defined above and $Y_2$ is a halogen atom to give the nitrogen-containing heterocyclic compound (I).

PROCEDURE C

A compound of the formula:

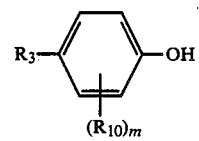

(VI)

wherein $R_3$, $R_{10}$ and m are each as defined above or its alkali metal salt is reacted with a compound of the formula:

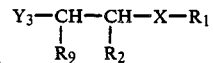

(VII)

wherein $R_1$, $R_2$, $R_9$ and X are each as defined above and $Y_3$ is a halogen atom, a mesyloxy group or a tosyloxy group to give the nitrogen-containing heterocyclic compound (I) wherein A is 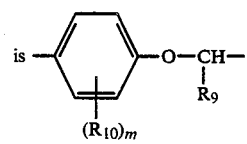

(in which $R_9$, $R_{10}$ and m are each as defined above).

PROCEDURE D

A compound of the formula:

    (VIII)

wherein $R_{11}$ is an alkyl group of 3 to 7 carbon atoms and $Y_4$ is a halogen atom, a mesyloxy group or a tosyloxy group is reacted with a compound of the formula:

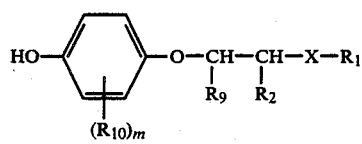    (IX)

wherein $R_1$, $R_2$, $R_9$, $R_{10}$, m and X are each as defined above or its alkali metal salt to give the nitrogen-containing heterocyclic compound (I) wherein $R_3$ is an alkoxy group and A is

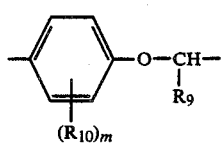

(in which $R_9$, $R_{10}$ and m are each as defined above).

In the above Procedures, the molar ratio of the reagents may be appropriately chosen. In Procedure A, the molar ratio of the compound (II) and the compound (III) is normally 1:1–10, preferably 1:1.1–1.5. In Procedure B, the molar ratio of the compound (IV) and the compound (V) is usually 1:0.5–10, preferably 1:0.8–2.0. In Procedure C, the molar ratio of the compound (VI) and the compound (VII) is ordinarily 1:0.5–2.0, especially 1:0.7–1.5. In Procedure D, the molar ratio of the compound (VIII) and the compound (IX) is usually 1:0.5–2.0, preferably 1:0.7–1.1.

Throughout Procedures A, B, C and D, the reaction may be normally carried out in the absence or presence of an inert solvent (e.g. dimethylformamide, dimethylsulfoxide, tetrahydrofuran, dimethoxyethane, toluene) in the existence of an acid binding agent. As the acid binding agent, there may be exemplified an alkali metal, an alkali metal hydride, an alkali metal amide, an alkali metal hydroxide, an alkali metal carbonate or an organic base (e.g. triethylamine, dimethylaniline). In order to accelerate the reaction, a phase transfer catalyst such as benzyltriethylammonium chloride, tetra-n-butylammonium bromide or tris(3,6-dioxaheptyl)amine may be employed. In this case, water is usable as the solvent.

The reaction is normally accomplished at a temperature of $-30°$ C. to the boiling temperature of the reaction mixture, preferably of room temperature to $110°$ C., within a period of 0.5 to 24 hours.

Recovery of the produced nitrogen-containing heterocyclic compound (I) from the reaction mixture and purification of the recovered nitrogen-containing heterocyclic compound (I) may be performed by per se conventional procedures. For instance, the recovery may be achieved by distillation, precipitation, extraction and the like. The purification can be achieved by recrystallization, chromatography, etc.

The nitrogen-containing heterocyclic compound (I) has optical isomers with respect to $R_2$, $R_5$, $R_7$, $R_8$ and/or $R_9$ and also geometrical isomers with respect to $R_6$. All of these isomers are included within the scope of the invention.

The compounds (III), (V), (VII) and (VIII) as the intermediates for production of the nitrogen-containing heterocyclic compound (I) are per se known or may be prepared by the known procedures or the similar methods thereto.

The compounds (II) and (IV) can be produced, for instance, according to the following scheme:

PROCEDURE (1)

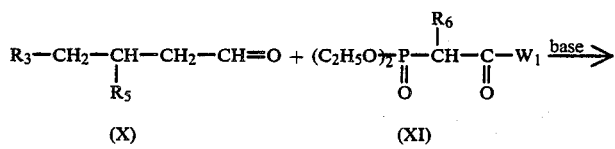

(X)    (XI)

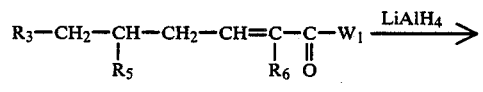

(XII)

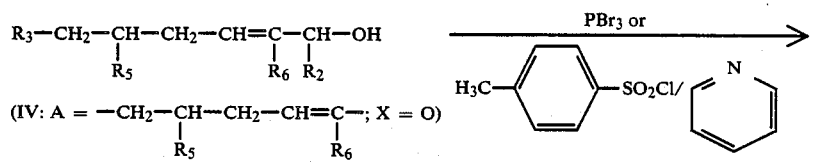

(IV: A = $-CH_2-CH-CH_2-CH=C-$; X = O)
           |              |
           $R_5$          $R_6$

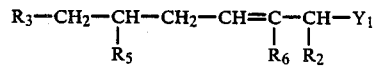

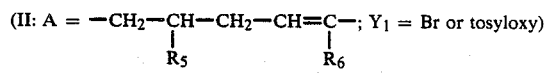

(II: A = $-CH_2-CH-CH_2-CH=C-$; $Y_1$ = Br or tosyloxy)
         |              |
         $R_5$          $R_6$ wherein $R_2$, $R_3$, $R_5$, $R_6$ and $Y_1$ are each as defined above and $W_1$ is a methyl group or a $C_1$–$C_4$ alkoxy group.

PROCEDURE (2)

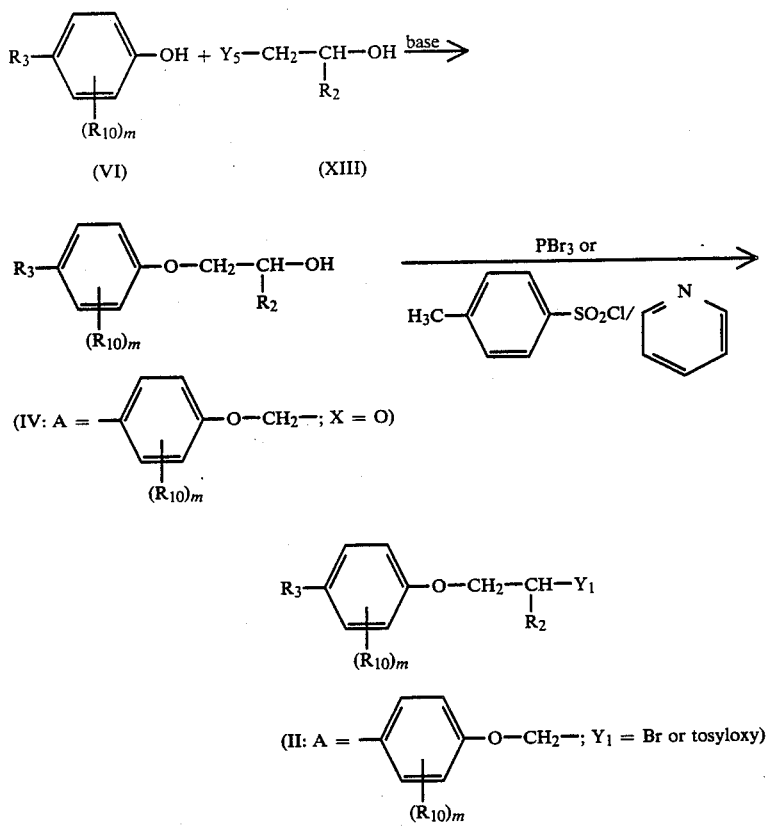

wherein $R_2$, $R_3$, $R_9$, $R_{10}$, m and $Y_1$ are each as defined above and $Y_5$ is a halogen atom.

The compound (VI) is known or can be prepared or by a per se conventional procedure (cf. Org. Synth., I, 150 (1941); Tetrahedron, 24, 2289 (1968); J. Org. Chem., 22, 1001 (1957)).

The compound (IX) is obtainable according to the following scheme:

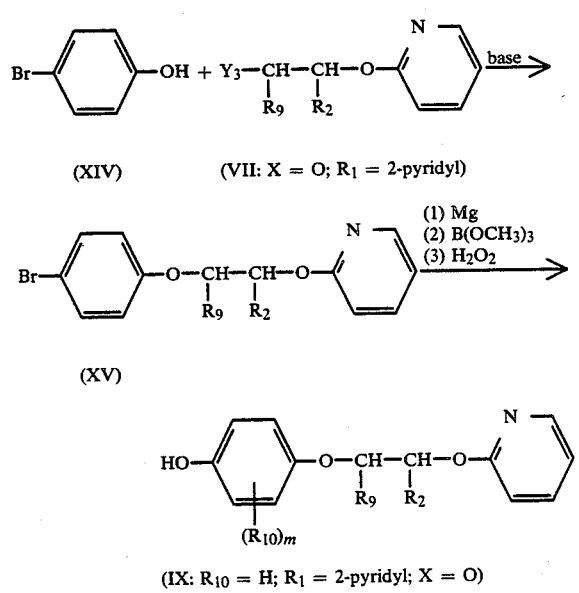

wherein $R_2$, $R_9$ and $Y_3$ are each as defined above.

Typical examples for preparation of the nitrogen-containing heterocyclic compound (I) are illustratively shown below.

EXAMPLE 1

Preparation of Compound No. 22 (Procedure A)

To a suspension of sodium hydride (0.032 g; 62% in oil) in anhydrous N,N-dimethylformamide (5 ml), a solution of 2-mercaptopyridine (0.093 g) in anhydrous N,N-dimethylformamide (3 ml) was dropwise added while stirring in 10 minutes, and stirring was continued at room temperature for 1 hour. The resultant mixture was cooled to a temperature of 5° to 10° C., and a mixture of 2-(4-isoamyloxyphenoxy)ethyl bromide (0.200 g) and anhydrous N,N-dimethylformamide (2 ml) was dropwise added thereto in 30 minutes, followed by stirring at room temperature overnight. The reaction mixture was poured into water (50 ml) and extracted with toluene (30 ml) two times. The extract was washed with water and dried over anhydrous sodium sulfate, and the solvent was removed by distillation under reduced pressure. The residue was purified by silica gel column chromatography to give the objective compound (0.120 g) as a colorless liquid. $n_D^{21.0} = 1.5670$.

EXAMPLE 2

Preparation of Compound No. 29 (Procedure B)

To a suspension of sodium hydride (0.086 g; 62% in oil) in anhydrous N,N-dimethylformamide (10 ml), a mixture of 2-(4-isobutoxymethylphenoxy)ethanol (0.500 g) and anhydrous N,N-dimethylformamide (5 ml) was dropwise added while stirring in 10 minutes, and stirring was continued at 60° to 70° C. for 2 hours. The resultant mixture was cooled to a temperature of 5° to 10° C., and a mixture of 2-bromothiazole (0.402 g) and anhydrous N,N-dimethylformamide (5 ml) was dropwise added thereto in 30 minutes, followed by stirring at room temperature overnight and further at 60° to 70° C. for 2 hours. The reaction mixture was poured into ice water (50 ml) and extracted with toluene (30 ml) two times. The extract was washed with water and dried over anhydrous sodium sulfate, and the solvent was removed by distillation under reduced pressure. The residue was purified by silica gel column chromatography to give the objective compound (0.164 g) as a colorless liquid. $n_D^{23.0} = 1.5403$.

EXAMPLE 3

Preparation of Compound No. 9 (Procedure C)

To a suspension of sodium hydride (0.070 g; 62% in oil) in anhydrous N,N-dimethylformamide (10 ml), a mixture of 4-n-butoxyphenol (0.300 g) and anhydrous N,N-dimethylformamide (5 ml) was dropwise added while stirring in 10 minutes. Stirring was continued at room temperature for 1 hour. The resulting mixture was cooled to a temperature of 5° to 10° C., and mixture of 2-(2-pyridyloxy)ethyl p-toluenesulfonate (0.529 g) and anhydrous N,N-dimethylformamide (5 ml) was dropwise added thereto in 30 minutes, followed by stirring at room temperature overnight and further at 60° to 70° C. for 2 hours. The reaction mixture was poured into ice water (50 ml) and extracted with toluene (30 ml) two times. The extract was washed with water and dried over anhydrous sodium sulfate, and the solvent was removed by distillation under reduced pressure. The residue was purified by silica gel column chromatography to give the objective compound (0.194 g) as white crystals. M.P., 53.2° C.

EXAMPLE 4

Preparation of Compound No. 7 (Procedure D)

To a suspension of sodium hydride (0.084 g; 62% in oil) in anhydrous tetrahydrofuran (10 ml), a mixture of 4-[2-(2-pyridyloxy)ethoxy]phenol (0.500 g) and anhydrous tetrahydrofuran (10 ml) was dropwise added while stirring in 30 minutes, and stirring was continued at room temperature for 1 hour. To the resultant mixture, a mixture of isoamyl bromide (0.425 g) and anhydrous tetrahydrofuran (5 ml) was dropwise added in 30 minutes, and stirring was continued at room temperature overnight, followed by heating under reflux for 1 hour. The reaction mixture was poured into ice water (50 ml) and extracted with toluene (30 ml) two times. The extract was washed with water and dried over anhydrous sodium sulfate, and the solvent was removed by distillation under reduced pressure. The residue was purified by silica gel column chromatography to give the objective compound (0.374 g) as white crystals. M.P., 69.1° C.

In the same manner as above, there were prepared the nitrogen-containing heterocyclic compounds (I), of which typical examples are shown in Table 1.

TABLE 1

$$R_3-A-\underset{R_2}{\overset{}{CH}}-X-R_1 \qquad (I)$$

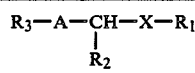

TABLE 1-continued $$R_3-A-CH(R_2)-X-R_1 \quad (I)$$

| Compound No. | R3 | A | R2 | X | R1 | Physical property |
|---|---|---|---|---|---|---|
| 7 | (CH3)2CH—CH2—CH2—O— | —C6H4—O—CH2— | H | O | 2-pyridyl | M.P., 69.1° C. |
| 8 | CH3—CH2—O— | —C6H4—O—CH2— | H | O | 2-pyridyl | M.P., 64.7° C. |
| 9 | CH3—CH2—CH2—CH2—O— | —C6H4—O—CH2— | H | O | 2-pyridyl | M.P., 53.2° C. |
| 10 | CH3—CH2—CH2—O— | —C6H4—O—CH2— | H | O | 2-pyridyl | M.P., 55.3° C. |
| 11 | CH3—(CH2)4—O— | —C6H4—O—CH2— | H | O | 2-pyridyl | $n_D^{26.5}$ 1.5350 |
| 12 | CH3—CH2—CH(CH3)—CH2—O— | —C6H4—O—CH2— | H | O | 2-pyridyl | M.P., 68.0° C. |
| 13 | (CH3)3C—CH2—CH2—O— | —C6H4—O—CH2— | H | O | 2-pyridyl | $n_D^{26.0}$ 1.5294 |
| 14 | (CH3)3C—CH2—O— | —C6H4—O—CH2— | H | O | 2-pyridyl | $n_D^{23.0}$ 1.5298 |
| 15 | (CH3)2CH—CH2—CH2—O— | —C6H4—O—CH2— | CH3 | O | 2-pyridyl | $n_D^{23.0}$ 1.5298 |
| 16 | (CH3)2CH—CH2—CH2—O— | —C6H4—O—CH2— | H | O | 2-thiazolyl | M.P., 69.4° C. |
| 17 | (CH3)2CH—CH2—CH2—O— | —C6H4—O—CH(CH3)— | H | O | 2-pyrimidinyl | $n_D^{22.5}$ 1.5304 |
| 18 | (CH3)2CH—CH2—CH2—O— | —C6H4—O—CH(CH3)— | H | O | 2-pyridyl | $n_D^{22.5}$ 1.5324 |

TABLE 1-continued $$R_3-A-CH(R_2)-X-R_1 \quad (I)$$

| Compound No. | R₃ | A | R₂ | X | R₁ | Physical property |
|---|---|---|---|---|---|---|
| 19 | CH₃−CH(CH₃)−CH₂−CH₂−O− | −C₆H₄−O−CH₂− (para) | CH₃ | O | 2-chloro-4-(−O−CH₂−)phenyl | $n_D^{22.5}$ 1.5324 |
| 20 | CH₃−CH(CH₃)−CH₂−CH₂−O− | −C₆H₄−O−CH₂− (para) | H | O | pyrimidin-2-yl | M.P., 97.2° C. |
| 21 | CH₃−CH(CH₃)−CH₂−CH₂−O− | −C₆H₄−O−CH₂− (para) | H | S | 4,5-dihydrothiazol-2-yl | $n_D^{21.5}$ 1.5674 |
| 22 | CH₃−CH(CH₃)−CH₂−CH₂−O− | −C₆H₄−O−CH₂− (para) | H | S | pyridin-2-yl | $n_D^{21.0}$ 1.5670 |
| 23 | CH₃−CH(CH₃)−CH₂−CH₂−O− | −C₆H₄−O−CH₂− (para) | H | S | pyrimidin-2-yl | $n_D^{22.0}$ 1.5657 |
| 24 | CH₃−CH(CH₃)−CH₂−CH₂−O− | −C₆H₄−O−CH(CH₃)− (para) | H | O | thiazol-2-yl | $n_D^{22.0}$ 1.5331 |
| 25 | CH₃−CH(CH₃)−CH₂−CH₂−O− | −C₆H₄−O−CH₂− (para) | CH₃ | O | thiazol-2-yl | $n_D^{22.5}$ 1.5281 |
| 26 | CH₃−CH(CH₃)−CH₂−CH₂−O− | −C₆H₄−O−CH₂− (para) | H | O | thiazol-2-yl | $n_D^{22.5}$ 1.5441 |
| 27 | CH₃O−C(CH₃)₂−CH₂−O− | −C₆H₄−O−CH₂− (para) | H | O | thiazol-2-yl | $n_D^{21.5}$ 1.5427 |
| 28 | CH₃−CH(CH₃)−CH₂−CH₂−O− | −C₆H₄−O−CH₂− (para) | H | O | pyridin-2-yl | $n_D^{23.0}$ 1.5348 |
| 29 | CH₃−CH(CH₃)−CH₂−CH₂−O− | −C₆H₄−O−CH₂− (para) | H | O | thiazol-2-yl | $n_D^{23.0}$ 1.5403 |
| 30 | CH₃−CH(CH₃)−CH₂−CH₂−O− | 2-Cl-C₆H₃-4-(−O−CH₂−) | H | O | thiazol-2-yl | $n_D^{23.0}$ 1.5488 |

TABLE 1-continued $$R_3-A-CH(R_2)-X-R_1 \quad (I)$$

| Compound No. | R₃ | A | R₂ | X | R₁ | Physical property |
|---|---|---|---|---|---|---|
| 31 | CH₃—CH(CH₃)—CH₂—CH₂—O— | 3,5-dimethylphenyl-O-CH₂— | H | O | -C(=N-CH₂-)S- (thiazoline) | $n_D^{23.0}$ 1.5300 |
| 32 | CH₃—CH(CH₃)—CH₂—CH₂—O— | 2-chlorophenyl-O-CH₂— | H | O | 2-pyridyl | $n_D^{23.0}$ 1.5440 |
| 33 | CH₃—CH(CH₃)—CH₂—CH₂—O— | 3,5-dimethylphenyl-O-CH₂— | H | O | 2-pyridyl | $n_D^{23.0}$ 1.5295 |
| 34 | CH₃—CH(CH₃)—CH₂—CH₂—CH₂— | phenyl-O-CH₂— | H | O | 2-pyridyl | M.P., 62.6° C. |
| 35 | CH₃—CH(CH₃)—CH₂—CH₂—CH₂— | phenyl-O-CH₂— | H | O | thiazoline | $n_D^{22.0}$ 1.5340 |

On the application of the nitrogen-containing heterocyclic compounds (I) as insecticidal agents, they may be used as such or preferably in any appropriate preparation form such as emulsifiable concentrates, dusts, granules, wettable powders and fine granules. The content of the nitrogen-containing heterocyclic compound (I) in such preparation is usually from about 0.1 to 99.9% by weight, preferably from about 2 to 80% by weight.

The preparation can be formulated in a per se conventional manner by mixing at least one of the nitrogen-containing heterocyclic compounds (I) with an appropriate solid or liquid carrier(s) or diluent(s). An appropriate adjuvant(s) (e.g. surfactants, adherents, dispersants, stabilizers) may be admixed therein for improving the dispersibility and other properties of the active ingredient on use.

Examples of the solid carriers or diluents are clays (e.g. kaolin, bentonite, fuller's earth, pyrophyllite, sericite), talcs, other inorganic materials (e.g. hydrated silica, pumice, diatomaceous earth, sulfur powder, active carbon), etc. in fine powders or in a powdery form. Examples of the liquid carriers or diluents are alcohols (e.g. methanol, ethanol), ketones (e.g. acetone, methyl ethyl ketone), ethers (e.g. diethyl ether, dioxane, cellosolve, tetrahydrofuran), aromatic hydrocarbons (e.g. benzene, toluene, xylene, methylnaphthalene), aliphatic hydrocarbons (e.g. gasoline, kerosene, lamp oil), esters, nitriles, acid amides (e.g. dimethylformamide, dimethylacetamide), halogenated hydrocarbons (e.g. dichloroethane, trichloroethylene, carbon tetrachloride), etc.

Examples of the surfactants are alkylsulfates, alkylsulfonates, alkylarylsulfonates, polyethylene glycol ethers, polyhydric alcohol esters, etc. Examples of the adherents and dispersants may include casein, gelatin, starch powder, CMC (carboxymethyl cellulose), gum arabic, alginic acid, ligninsulfonate, bentonite, molasses, polyvinyl alcohol, pine oil and agar. As the stabilizers, there may be used PAP (isopropyl acid phosphates mixture), TCP (tricresyl phosphate), tolu oil, epoxydized oil, various surfactants, various fatty acids and their esters, etc.

In addition, the preparation may contain insecticides, insect growth inhibitors, acaricides, nematocides, fungicides, herbicides, plant growth regulators, fertilizers, soil improvers, etc. Particularly when employed in conjunction with conventional insecticides, a broad spectrum of activity or a more immediate effect on very heterogeneous populations is provided. Examples of the insecticides include organic phosphorus compounds (e.g. fenitrothion (O,O-dimethyl-O-(3-methyl-4-nitrophenyl)phosphorothioate), malathion (S-[1,2-bis(ethoxycarbonyl)ethyl]O,O-dimethylphosphorothiote), dimethoate (O,O-dimethyl-S-(N-methylcarbamoylmethyl)phosphorodithioate), salithion (2-methoxy-4H-1,3,2-benzdioxaphosphorin-2-sulfide), diazinon (O,O-diethyl-O-(2-isopropyl-6-methyl-4-pyrimydinyl)phosphorothioate), dipterex (2,2,2-trichloro-1-hydroxyethyl-O,O-dimethylphosphonate), dichlorvos (O-(2,2-dichlorovinyl)-O,O-dimethylphosphate), etc.), carbamate compounds (e.g. MPMC (3,4-dimethylphenyl N-methylcarbamate), MTMC (m-tolyl N-methylcarbamate), BPMC (2-sec-butylphenyl N-methylcarbamate), carbaryl (1-naphthyl N-methylcarbamate), etc.) and pyrethroid compounds (e.g. resmethrin (5-benzyl-3-furylmethyl-d,l-cis,trans-chrysanthemate), permethrin (3-phenoxybenzyl-d,l-cis,trans-3-(2,2-dichlorovinyl)-2,2-dimethylcyclopropanecarboxylate), fenpropathrin (α-cyano-3-phenoxybenzyl 2,2,3,3-tetramethylcyclopropanecarboxylate), fenvalerate (α-cyano-m-phenoxybenzyl α-isopropyl-p-chlorophenylacetate), etc.).

The nitrogen-containing heterocyclic compounds (I) of the invention formulated into an appropriate composition may be applied in a suitable application method such as spraying, smoking, soil treatment, soil surface treatment or in combination with animal feed. For instance, when the nitrogen-containing heterocyclic compounds (I) are added to the feed for silkworms, enlargement of cocoon is expected.

Some practical embodiments of the composition for the control of insects according to the invention are illustratively shown in the following Formulation Examples wherein % and part(s) are by weight.

FORMULATION EXAMPLE 1

Each of Compound Nos. 1 to 35 (20 parts), an emulsifier (a mixture of polyoxyethylene-styrenated phenyl ether, polyoxyethylene-styrenated phenyl ether polymer and an alkylarylsulfonate) (20 parts) and xylene (60 parts) are mixed well to make an emulsifiable concentrate.

FORMULATION EXAMPLE 2

Each of Compound Nos. 1 to 35 (20 parts) and an emulsifier (sodium laurylsulfate) (5 parts) are mixed well, and diatomaceous earth (300 mesh) (75 parts) is added thereto, and the resultant mixture is mixed well in a pulverizer to make a wettable powder.

FORMULATION EXAMPLE 3

Each of compound Nos. 16, 28 or 29 (3 parts) is dissolved in acetone (20 parts), talc (300 mesh) (97 parts) is added thereto, and the resultant mixture is mixed well in a pulverizer. Then, acetone is eliminated by evaporation to give a dust.

FORMULATION EXAMPLE 4

Each of Compound Nos. 28 or 29 (5 parts), a dispersant (calcium ligninsulfonate) (2 parts) and clay (93 parts) are mixed well in pulverizer. To the resultant mixture, water is added in an amount of 10%, and the resulting mixture is kneaded well and granulated by the aid of a granulator, followed by drying to give granules.

FORMULATION EXAMPLE 5

Compound No. 29 (2 parts), a dispersant (calcium lingninsulfonate) (2 parts) and clay (96 parts) are mixed well in a pulverizer. Water is added to the resultant mixture in an amount of 10%. The resulting mixture is mixed well and granulated by the aid of a granulator, followed by air-drying to give fine granules.

FORMULATION EXAMPLE 6

Each of Compound Nos. 1 to 35 (10 parts), resmethrin (20 parts), an emulsifier (a mixture of polyoxyethylene-styrenated phenyl ether, polyoxyethylene-styrenated phenyl ether polymer and an alkylarylsulfonate) (20 parts) and xylene (50 parts) are mixed well to make an emulsifiable concentrate.

FORMULATION EXAMPLE 7

Each of Compound Nos. 1 to 35 (10 parts), fenitrothion (20 parts) and an emulsifier (sodium laurylsulfate) (5 parts) are mixed well, and diatomaceous earth (300 mesh) (65 parts) is added thereto, and the resultant mixture is mixed well in a pulverizer to make a wettable powder.

The following Examples show some typical test data indicating the excellent insect control activity of the nitrogen-containing heterocyclic compounds (I). The compounds used for comparison are as follows:

| Compound No. | Chemical structure | Remarks |
|---|---|---|
| (a) | 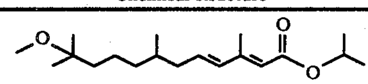 | Known as "methoprene"; U.S. Pat. Nos. 3,904,662 & 3,912,815 |

TEST EXAMPLE 1

An emulsifiable concentrate prepared according to Formulation Example 1 was diluted with water to make a 400 fold dilution. The dilution (0.7 ml) was added to 100 ml of distilled water. Last instar larvae of common mosquito (*Culex pipiens pallens*) were released therein and reared for 7 days until their emergence. The rate of emergence was observed according to the following criteria:

A: less than 10%
B: between 10 and 90%
C: more than 90%

The results are shown in Table 2.

TABLE 2

| Test compound No. | Concentration (ppm) | Rate of emergence (%) |
|---|---|---|
| 1 | 3.5 | A |
| 2 | 3.5 | A |
| 3 | 3.5 | A |
| 4 | 3.5 | A |
| 5 | 3.5 | A |
| 6 | 3.5 | A |
| 7 | 3.5 | A |
| 8 | 3.5 | A |
| 9 | 3.5 | A |
| 10 | 3.5 | A |
| 11 | 3.5 | A |
| 12 | 3.5 | A |
| 13 | 3.5 | A |
| 14 | 3.5 | A |
| 15 | 3.5 | A |
| 16 | 3.5 | A |
| 17 | 3.5 | A |
| 18 | 3.5 | A |
| 19 | 3.5 | A |
| 20 | 3.5 | A |

TABLE 2-continued

| Test compound No. | Concentration (ppm) | Rate of emergence (%) |
| --- | --- | --- |
| 21 | 3.5 | A |
| 22 | 3.5 | A |
| 23 | 3.5 | A |
| 24 | 3.5 | A |
| 25 | 3.5 | A |
| 26 | 3.5 | A |
| 27 | 3.5 | A |
| 28 | 3.5 | A |
| 29 | 3.5 | A |
| 30 | 3.5 | A |
| 31 | 3.5 | A |
| 32 | 3.5 | A |
| 33 | 3.5 | A |
| 34 | 3.5 | A |
| 35 | 3.5 | A |
| (a) | 3.5 | A |
| Untreated | — | C |

TEST EXAMPLE 2

Powdered animal feed (2 g) was thoroughly mixed with bran (14 g). An emulsifiable concentrate prepared according to Formulation Example 1 was diluted with water to a designed concentration and the dilution was added to the above mixture. The resultant mixture was stirred well to make an artificial culture. Thirty larvae of housefly (*Musca domestica*) were reared therein until their pupation. The obtained pupae were placed into a plastic cup, and the rate of emergence was determined. According to the following equation, the emergence inhibition (%) was calculated:

Emergence inhibition % =

$$\left(1 - \frac{\text{Rate of emergence in treated plot}}{\text{Rate of emergence in untreated plot}}\right) \times 100$$

The results are shown in Table 3.

TABLE 3

| Test compound No. | Emergence inhibition (%) | | |
| --- | --- | --- | --- |
| | 3 ppm | 1 ppm | 0.3 ppm |
| 2 | 100 | 42 | 3 |
| 7 | 100 | 87 | 31 |
| 12 | 83 | 20 | 0 |
| 15 | 93 | 43 | 0 |
| 16 | 100 | 96 | 45 |
| 25 | 100 | 58 | 8 |
| 26 | 100 | 61 | 11 |
| 28 | 100 | 100 | 93 |
| 29 | 100 | 100 | 100 |
| 32 | 94 | 56 | 3 |
| 34 | 100 | 67 | 41 |
| 35 | 100 | 100 | 51 |
| (a) | 60 | 13 | 2 |

What is claimed is:

1. A nitrogen-containing heterocyclic compound of the formula:

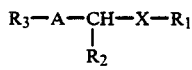

wherein $R_1$ is a group of the formula:

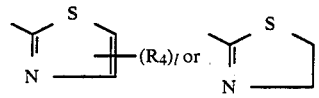

wherein
$R_4$ is a hydrogen atom, a halogen atom or a methyl group and $l$ is an integer of 1 or 2;
$R_2$ is a hydrogen atom or a methyl group;
$R_3$ is an alkyl group, an alkoxy group, an alkenyl group or an alkenyloxy group, all of which may be optionally substituted with one or more substituents selected from the group consisting of lower alkoxy, halo(lower)alkoxy, halogen, nitro and amino;
A is one of the following groups:

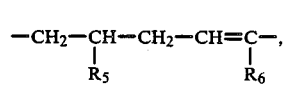

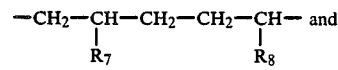

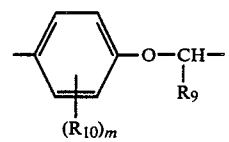

wherein $R_5$, $R_6$, $R_7$, $R_8$ and $R_9$ are the same or different and are each a hydrogen atom or a methyl group, $R_{10}$ is a hydrogen atom, a halogen atom or a lower alkyl group and m is an integer of 1 to 4; and X is an oxygen atom or a sulfur atom.

2. The nitrogen-containing heterocyclic compound according to claim 1, wherein $R_3$ is a $C_1$-$C_7$ alkyl group, a $C_2$-$C_7$ alkoxy group or a $C_3$-$C_7$ alkenyloxy group, wherein said $C_1$-$C_7$ alkyl or $C_2$-$C_7$ alkoxy groups are optionally substituted with one or more alkoxy groups.

3. The nitrogen-containing heterocyclic compound according to claim 1, which is represented by the formula:

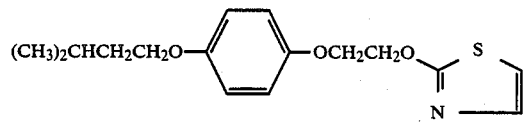

4. The nitrogen-containing heterocyclic compound according to claim 1, which is represented by the formula:

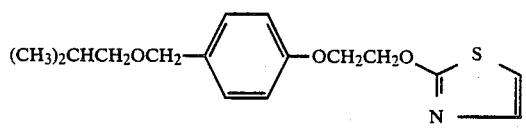

5. The nitrogen-containing heterocyclic compound according to claim 1, which is represented by the formula:

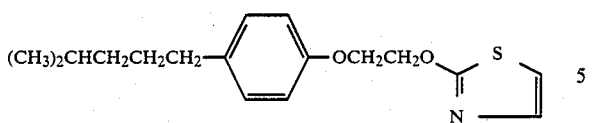

6. The nitrogen-containing heterocyclic compound according to claim 1, wherein R₃ is

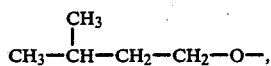

A is

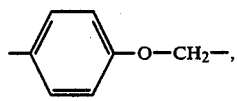

R₂ is H, X is S and R₁ is

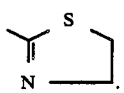

7. The nitrogen-containing heterocyclic compound according to claim 1, wherein R₃ is

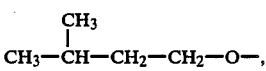

A is

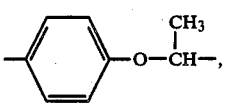

R₂ is H, X is O and R₁ is

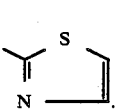

8. The nitrogen-containing heterocyclic compound according to claim 1, wherein R₃ is

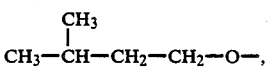

A is

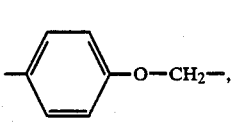

R₂ is CH₃, X is O and R₁ is

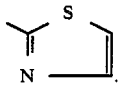

9. The nitrogen-containing heterocyclic compound according to claim 1, wherein R₃ is

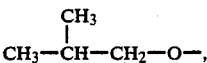

A is

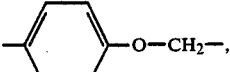

R₂ is H, X is O and R₁ is

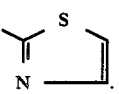

10. The nitrogen-containing heterocyclic compound according to claim 1, wherein R₃ is

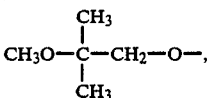

A is

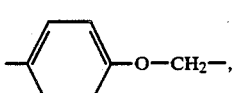

R₂ is H, X is O and R₁ is

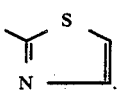

11. The nitrogen-containing heterocyclic compound according to claim 1, wherein R₃ is

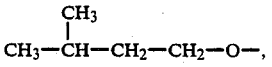

A is

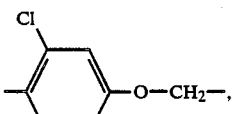

R₂ is H, X is O and R₁ is

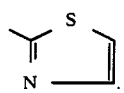

12. The nitrogen-containing heterocyclic compound according to claim 1, wherein $R_3$ is

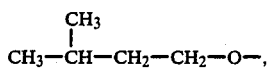

A is

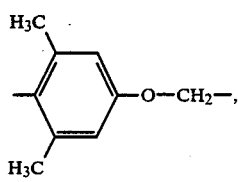

$R_2$ is H, X is O and $R_1$ is

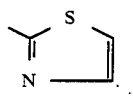

13. A composition for preventing or exterminating insects which comprises as an active ingredient an insecticidally effective amount of the compound according to claim 1, and an inert carrier or diluent.

14. A method for preventing or exterminating insects which comprises applying an insecticidally effective amount of the compound according to claim 1 to the insects.

15. A composition for preventing or exterminating insects which comprises as an active ingredient an insecticidally effective amount of the compound according to claim 2, and an inert carrier or diluent.

16. A method for preventing or exterminating insects which comprises applying an insecticidally effective amount of the compound according to claim 2.

* * * * *